United States Patent [19]

Lauks et al.

[11] Patent Number: 4,864,229

[45] Date of Patent: Sep. 5, 1989

[54] METHOD AND APPARATUS FOR TESTING CHEMICAL AND IONIC SENSORS

[75] Inventors: Imants R. Lauks, Morrisville, Pa.; Henry J. Wieck, Brooklyn, N.Y.

[73] Assignee: Integrated Ionics, Inc., Dayton, N.J.

[21] Appl. No.: 230,656

[22] Filed: Aug. 5, 1988

Related U.S. Application Data

[63] Continuation of Ser. No. 859,293, May 5, 1986, abandoned.

[51] Int. Cl.$^4$ ............................................. G01N 27/00
[52] U.S. Cl. ................... 324/158 F; 73/1 R; 73/1 G
[58] Field of Search .............. 73/1 R, 1 G, 23, 26, 73/864.81, 864.83; 204/1 T, 400, 401, 406, 415, 416, 418, 419; 324/71.1, 71.5, 158 F, 158 R; 357/25; 364/571

[56] References Cited

U.S. PATENT DOCUMENTS

| | | | |
|---|---|---|---|
| 2,940,041 | 6/1960 | Jacobson | 357/25 X |
| 4,089,058 | 5/1978 | Murdock | 364/571 |
| 4,437,969 | 3/1984 | Covington et al. | 357/25 X |
| 4,462,246 | 7/1984 | Advani et al. | 73/23 |
| 4,539,092 | 9/1985 | Morgan | 204/415 |
| 4,560,464 | 12/1985 | Lieber | 204/400 X |
| 4,618,929 | 10/1986 | Miller et al. | 128/635 |
| 4,627,893 | 12/1986 | Cormier et al. | 73/1 R X |
| 4,641,249 | 2/1987 | Gion et al. | 324/438 X |

*Primary Examiner*—Jerry Smith
*Assistant Examiner*—Stephen M. Baker
*Attorney, Agent, or Firm*—Pennie & Edmonds

[57] ABSTRACT

A method and apparatus for automatically testing chemical and ionic sensing electronic circuits is provided. A fluid used in testing is placed in a hollow pipette with at least one open end. The open end of the pipette is applied directly against a sensing layer on the sensing electronic circuit forming a leakproof seal. Alternatively, a flow-through type fluid container is used and is advantageously applied with gas measurements. Test electronics are provided to compile and analyze the performance of various sensing layers. Aligning means automatically select a sensing electronic circuit and position the circuit such that the holding device can be urged against the sensing layer automatically.

22 Claims, 3 Drawing Sheets

METHOD AND APPARATUS FOR TESTING CHEMICAL AND IONIC SENSORS

This is a continuation, of application Ser. No. 859,293, filed May 5, 1986, abandoned.

CROSS-REFERENCE TO RELATED APPLICATIONS

Related applications are Application Ser. Nos. 572,182, abandoned, and 572,185, U.S. Pat. No. 4,739,380, assigned to the present assignee, which are incorporated herein by reference.

BACKGROUND OF THE INVENTION

This relates to ambient sensing devices such as ion sensitive and chemically sensitive devices and to methods of testing such devices in appropriate environments.

It frequently is desirable to monitor the composition of the chemical environment, for example, to regulate chemical or biochemical processes, to determine air or water quality, or to measure parameters of interest in biomedical, agricultural or animal husbandry disciplines.

Because of the nature of the chemical environment, it is desirable that any measurement apparatus have at least some of the properties of: low cost, simple fabrication methodology, digital operation, some degree of signal preconditioning or intelligence, small size, high chemical sensitivity with selectivity, multiple species information with specificity, choice of reversible or integrating response to chemical species, temperature insensitivity or compensation and low power operation. In addition, the measurement apparatus should have good long term electrochemical stability, good physical resiliency and strength and good resistance to corrosion and chemical attack. In the case of electrical measurement devices, the devices should also have low electrical impedance to provide good signal to noise ratios. With chemically sensitive devices, the devices should also have a Nerstian response to the chemical phenomena being measured.

One method for the detection, measurement and monitoring of the chemical properties of a substance involves the measurement of an electric potential where the potential is dependent upon the chemical activity being measured. Bergveld has proposed that hydrogen and sodium ion activities in an aqueous solution be measured by a metal oxide semiconductor field-effect transistor (MOSFET) modified by removal of the gate metal. P. Bergveld, "Development, Operation, and Application of the Ion-Sensitive Field-Effect Transistor as a Tool for Electrophysiology" *IEEE Transactions of Biomedical Engineering*, Vol. BME-19, pages 342–351 (September, 1972). In particular, if a MOSFET with no gate metal were placed in an aqueous solution, Bergveld suggested that the silicon dioxide insulation layer would become hydrated and then, because of impurities in the hydrated layer, ion selective. After hydration of the insulation layer of the MOSFET, Bergveld believed the device could be used for ion activity measurement by immersing the device in the solution in question and then recording conductivity changes of the device. Thus, the Bergveld device is commonly referred to as an ion-sensitive field effect transistor (ISFET).

Bergveld's work led to other developments in the field of ion sensitive electrodes such as the chemical sensitive field effect transistor (CHEMFET) device described in U.S. Pat. No. 4,020,830 which is incorporated herein by reference. As described in the '830 patent, the CHEMFET is a MOSFET in which the gate metal has been replaced by a chemically sensitive system that is adapted to interact with certain substances to which the system is exposed. Thus as shown in FIGS. 1 and 2 of the '830 patent, the CHEMFET is identical in structure to a MOSFET except for a sensing layer or membrane 38 that is deposited in place of a metal gate layer on the oxide insulator above the channel region of the transistor and, optionally, an impervious layer 44 that covers all other parts of the CHEMFET that might be exposed to the solution. Numerous variations on CHEMFET structures are disclosed, for example, in U.S. Pat. Nos. 4,180,771, 4,218,298, 4,232,326, 4,238,757, 4,305,802, 4,332,658, 4,354,308, 4,485,274 and 4,397,714, and in the assignee's above-identified applications.

The concept of an ISFET or CHEMFET is especially attractive because of the promise it holds that the high volume, low cost fabrication techniques that are used to manufacture field effect transistors (FETs) in integrated circuits may somehow be adapted for the manufacture of ISFETs and CHEMFETs. Advances in such technology are disclosed, for, example, in the above-referenced Application Ser. Nos. 572,182 and 572,185.

One problem encountered in the fabrication of integrated circuits (ICs) is the testing of such devices. Because integrated circuits are so small and yet so complicated, testing imposes major problems in the handling of ICs and in the design of appropriate testing devices and protocols. At the same time, testing is needed as a process control to ensure that the IC manufacturing process is operating as desired and to identify the inevitable numbers of ICs that do not meet specifications for whatever reason. Testing is a particular problem in the manufacture of ISFETs and CHEMFETs since these devices are transducers which convert environmental variables to an electrical signal. Complete testing of such devices requires that the testing be carried out by exposing the ion sensing or chemical sensing layer of these devices to the environment which the ISFETs and CHEMFETs are designed to measure.

SUMMARY OF THE INVENTION

In accordance with the present invention, a method and apparatus are provided for automatically testing chemical and ionic sensing electronic circuits such as ISFETs and CHEMFETs. Such circuits are tested efficiently through the use of test electronics and an automatically controlled test fluid interface. Circuits which do not conform to desired electrical criteria may be automatically altered so as to conform.

In the preferred embodiment of the invention, the test electronics include a plurality of probes for contacting test points on the electronic circuit under test and a microprocessor for performing a series of tests on the circuit efficiently and automatically. The microprocessor may further be programmed with characteristics of a number of sensing circuits and test fluids against which the measured data of the circuit under test are compared.

The apparatus of the present invention further comprises a fluid holding device for holding a test fluid and a positioning means for automatically urging the holding device against a sensing layer of the circuit under test. The positioning means requires at least one axis of motion. In the preferred embodiment of the invention, this axis is essentially linear in a direction perpendicular to the plane of the circuit under test. The positioning means is controlled by the test electronics. Means are also provided to automatically select different holding devices as well as automatically filling and discharging the holding device.

In a preferred embodiment of the invention, the holding device comprises a tank that is open at its upper and lower ends. The open lower end of the holding device is directly placed on the sensing layer by the positioning means, thus forming a leakproof seal. To insure a leakproof seal, a sealing material may be placed at the area of contact between the wall of the holding device and the sensing layer. A test fluid is then inserted into the holding device through its open upper end. Alternatively, in another embodiment of the invention, the holding device comprises at least a hydrophobic surface to constrain the test fluid to the sensing layer and thereby prevent flow of the test fluid to other regions of the circuit under test.

Gases, non-homogeneous solutions, solutions in which measurements must be taken at various temperatures or pressures, and solutions whose compositions need to be varied during test measurements may be advantageously measured by a flow-through container in which the fluid constantly flows over the sensing layer. Such a flow-through container comprises a holding device shaped in the form of a trough with an open bottom end for contacting the sensing layer of the circuit under test and inlet and outlet ports through which the test fluid flows.

BRIEF DESCRIPTION OF THE DRAWINGS

These and other objects, features and advantages of the invention will be more readily apparent from the following detailed description of preferred embodiments of the invention, which is provided by way of illustration, in which.

DETAILED DESCRIPTION OF THE INVENTION

Figure 1:
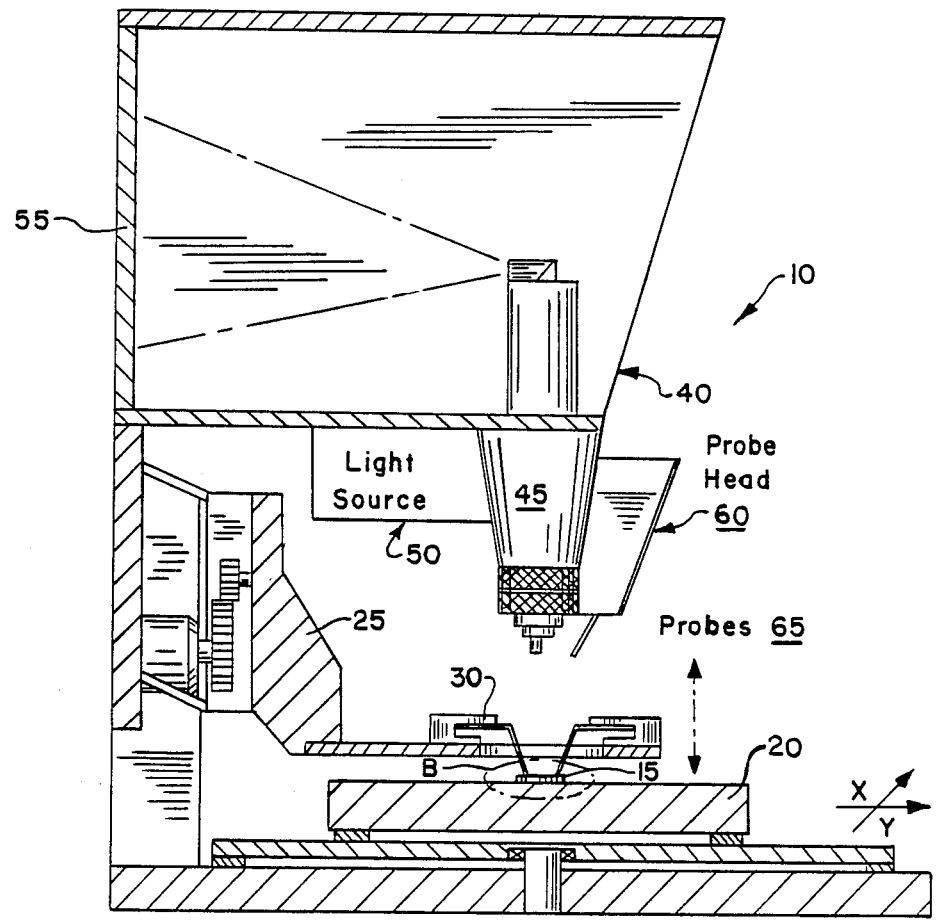
FIG. 1 is a side view partially in cross section of an illustrative prior art IC test device.

FIG. 1 depicts an illustrative IC test probe and alignment apparatus 10 as described in U.S. Pat. No. 4,266,191. Such apparatus is used for the alignment of integrated circuits 15 for testing. The apparatus includes an x-y positioning table 20, means (not shown) for adjusting the position of the table in the x and y directions, means 25 for adjusting the vertical position of the table, an integrated circuit chip carrier 30 mounted on the x-y table, viewing optics 40 comprising a microscope 45, a light source 50 and a projection screen 55, and a probe head 60 from which extend needle-like probes 65 for contacting test points on the integrated circuit or circuits being tested.

Figure 2:
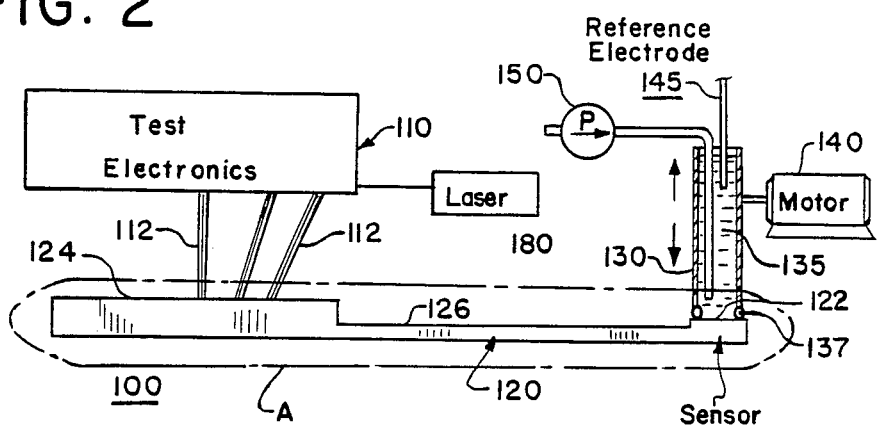
FIG. 2 is a schematic illustration of a preferred embodiment of the present invention.

As shown in FIG. 2 and described in more detail below, an apparatus 100 is provided for automatically testing chemical and ionic sensing electronic circuits 120. Apparatus 100 comprises a probe head 110, a fluid holding device 130, a device positioning motor 140, a reference electrode 145 and a pump means 150 for filling fluid into holding device 130 and removing it therefrom. An array of needle-like probes 112 extend from probe head 110 to contact test points on circuit 120.

Advantageously, the apparatus of FIG. 2 is mounted in a conventional IC test probe and alignment device such as that shown in FIG. 1. The area defined by the dotted line A of FIG. 2 corresponds approximately to the area defined by the dotted line B of FIG. 1.

As shown, the apparatus of the present invention is advantageously used in testing an extended gate field effect transistor (EGFET) such as that disclosed in the above-referenced Application Ser. No. 572,182. In such a circuit, a sensing layer 122 is physically offset from the rest of the circuit, and in particular, physically offset from transistor circuitry 124 to which the sensing layer is coupled by a guarded signal line 126. The invention may also be practiced with other designs of ISFETs and CHEMFETs as well.

Probe head 110 contains test electronics that conduct measurements such as measurements of voltage or current flow through various portions of circuit 120 and compile and analyze the resulting data. In accordance with the invention at least some of these measurements are made while sensing layer 122 is in contact with a test fluid contained in holding device 130. Holding device 130 illustratively is a glass pipette with open upper and lower ends. Positioning motor 140 raises and lowers the holding device so as to permit removal and replacement of the electronic circuit that is being tested.

In practicing the invention, the positioning motor secures the fluid holding device against the continuous upper surface of sensing layer 122 so as to establish a leakproof seal. Thereafter, a test fluid is poured into the fluid device, as a result of which it contacts the upper surface of sensing layer 122 through the open lower end of the fluid holding device. The reference electrode 145 is also brought into contact with the test fluid so as to provide a reference potential. The specific reference electrode 145 used depends on the test solution used. Advantageously, the reference electrode 145 should be the same type of electrode that would be used with the sensing layer in normal use when monitoring the fluids the sensing layer was designed to monitor.

As in the prior art, alignment of the electronic circuit and the sensing layer with respect to the microscope and fluid holding device is accomplished by means of an x-y positioning table. Alignment of the needle-like probes 112 of probe head 110 with appropriate test points on the electronic circuit is accomplished by an independent x-y alignment device (not shown). Illustrative publications describing appropriate alignment devices are U.S. Pat. No. 4,219,110, Wafer Probe Apparatus with Pneumatic Water Orienting Mechanism (orienting a semiconductor wafer on a table by pressurized gas and LED phototransistor combinations); Weiss, Aaron, "Update on Wafer Probing Systems and Accessories" *Semiconductor International* Vol. 5, No. 5 (May 1982) pp 67–78 (laser based pattern recognition, general type pattern recognition, feature extraction pattern recognition, optical encoder controlled X-Y tables, linear reluctance positioners, lead screw X-Y tables, and X-Y-Z tables); and Geary, J., "Cryogenic Wafer Prober for Josephson Devices" *IEEE Transactions on Magnetics*, Vol. Mag-19, No. 3, (May 1983) pp 1190–1192 (stepper motors) which are incorporated herein by reference.

In the preferred embodiment of the present invention, a microprocessor in the test electronics is utilized to perform various tests and compile data automatically from a plurality of test fluids of different concentrations. The response of the circuit to known concentrations of test fluid is measured. This response is compared to theoretical or desired responses, for example, a linear response to a series of linearly varying test fluid concentrations. Calibration data for known sensing probes and fluids are stored in system memory.

Blakeslee, Douglas, "Techniques for Wafer Analysis of LSI/VLSI Devices", *New Electronics*, Vol. 16, No. 19, (Oct. 4, 1983) pp 55-61, incorporated herein by reference, sets forth some available software for the management of sensing probe test procedures.

Advantageously, the automatic test apparatus comprises a laser 180 which automatically trims portions of the sensing layer in order to bring the output electrical characteristics within a predetermined desired range specific to that particular device and test solution. Alternatively, other portions of the circuit under test may be laser trimmed or cut in dimension such that uniform electrical output is obtained. Such laser trimming of semiconductor devices to bring output electrical characteristics within a predetermined range is known to those skilled in the art. In another embodiment, the circuit under test contains a programmable read only memory (PROM) into which is programmed a correction curve for the sensor's characteristic response as measured by the automatic test equipment.

In all embodiments of the present invention, a proper interface between the holding device 130, sensing layer 122 and solution 135 of FIG. 2 is desirable for efficient operation. Such an interface may be constructed in a number of ways.

The device as depicted in FIG. 2 comprises a hollow holding device 130 into which the solution to be tested is placed. The holding device 130 is open at the end with which it interfaces the sensing layer 122. In a preferred embodiment of the invention, the open end of the holding device interfaces in a planar manner with an essentially flat continuous sensing layer so that there is substantially continuous contact between the holding device and the sensing layer while the sensing layer provides a continuous (i.e., unperforated) surface that serves as the bottom of the fluid holding device. The area of contact between the holding device and the sensing layer may be coated with a sealing material so as to assure a tight, leakproof fit. Such a sealing layer 137 of material may also serve to prevent damage to a sensing layer which is fragile or otherwise prone to breakage. Alternatively, a hydrophobic surface may be used on the holding device to confine the test fluid to the sensing layer and thereby prevent flow of the test fluid to other portions of the circuit.

Figure 3:
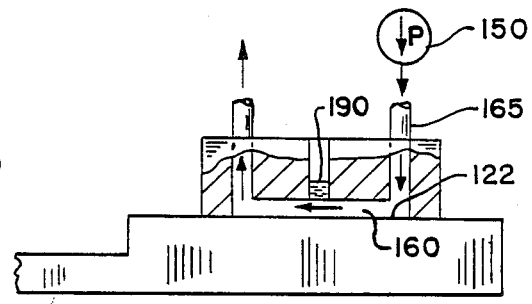
FIG. 3 is a schematic illustration of a flow-through container of the present invention.

In a further embodiment, as depicted in FIG. 3, a flow-through type of container 160 is provided having a fluid passage 165 and a reference electrode 190. Such an embodiment is advantageously used with an external fluid handling system (not shown) comprising a fluid sampling valve, pump 150 and a plurality of fluid containers to bring fluids of differing compositions, pressures, temperatures and/or concentrations to the sensing layer in a predetermined sequence in a flow-through mode. Such a system permits construction of a calibration table of, for example, chemical concentration versus electrical output of the sensor.

Figure 4:
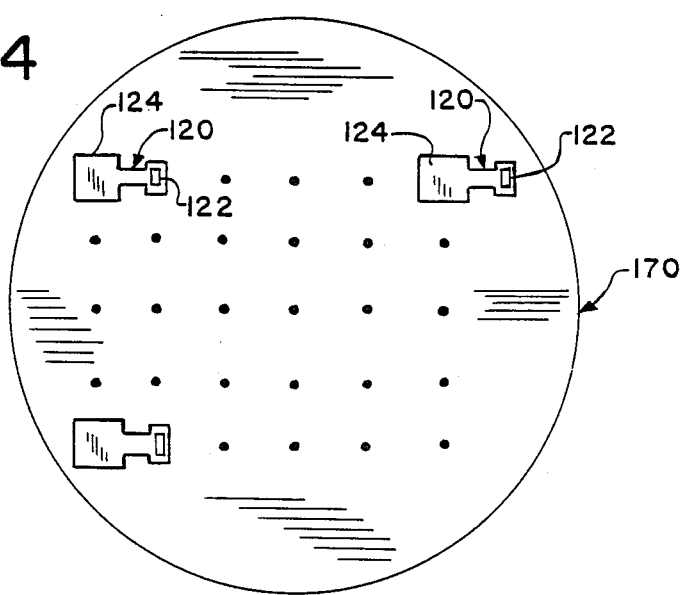
FIG. 4 is a top view of typical sensing probes to be tested.

FIG. 4 depicts a plurality of sensing circuits 120 disposed on a semiconductor wafer 170 in the form in which they are fabricated. Each circuit comprises electronics 124, signal line 126 and sensing layer 122. Upon completion of all tests on a single circuit, wafer 170 is moved by the aligning means to place the sensing layer of the next sensing circuit directly under the holding device.

Figure 5:
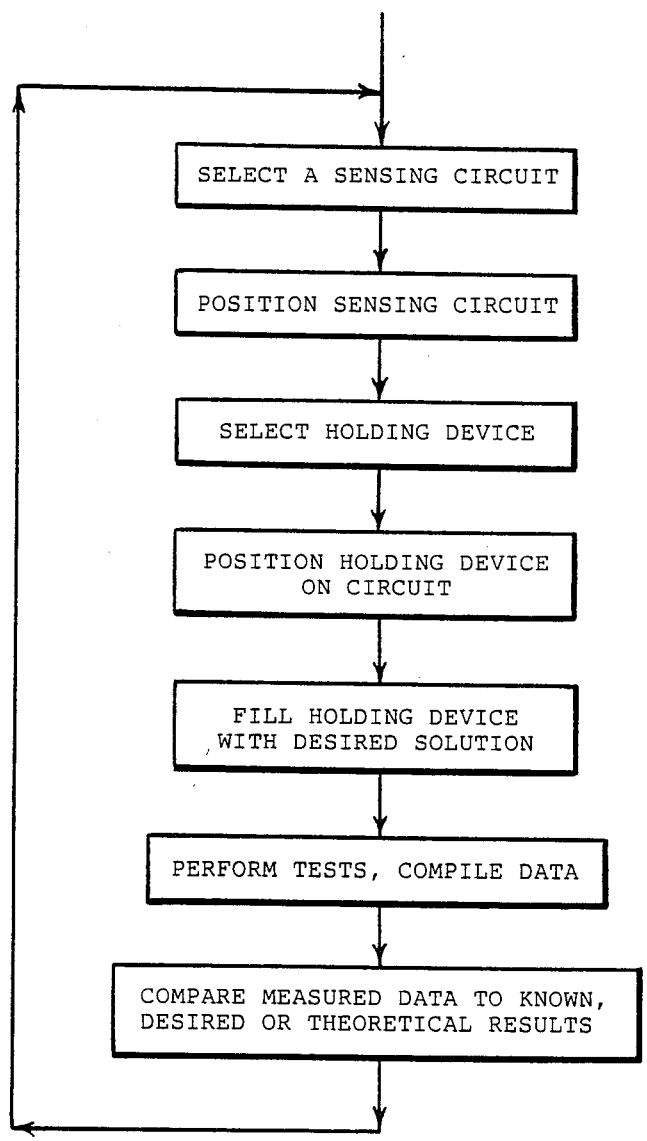
FIG. 5 is a flowchart of the testing process of the present invention.

FIG. 5 is a flowchart of the various processes performed by the preferred embodiment.

The method and apparatus disclosed can be implemented or engineered in a number of ways. The description is intended to illustrate the principles and mode of operation of the device and not to rigidly define the structure or process. Alternative methods and devices may be applicable without departing from the scope and spirit of the claims. For example, a pipette cylindrical in shape may be interfaced with a planar, convex, or concave sensing layer. Further, the sensing layer may not necessarily be physically offset from the electronics, or may exist within a cap which can be screwed or clamped onto the holding device.

What is claimed is:

1. Apparatus for automatically testing a plurality of chemical and ionic sensing electronic circuits comprising:
   a fluid confining cell having at least one open orifice to contain a known test fluid,
   means for receiving a first sensing electronic circuit device of a plurality of such sensing electronic circuit device on a continuous surface, in which said means for receiving comprises an exposed sensing layer to be tested, and for aligning said circuit device such that said sensing layer is aligned with said orifice in said fluid confining cell,
   positioning means for urging the open orifice of said fluid confining cell into leakproof engagement with said sensing electronic circuit device to be tested,
   wherein when said cell is filled with said known test fluid, said test fluid contacts said exposed sensing layer, and
   means for monitoring the response of said circuit device to said test fluid,
   wherein said aligning means automatically selects and positions in succession a plurality of sensing electronic circuit devices on said continuous surface with respect to said positioning means.

2. The apparatus of claim 1 wherein said means for monitoring the response of said circuit device to said test fluid comprises means for applying a test signal to said circuit while said exposed sensing layer is in contact with said test fluid; and for monitoring the response of said circuit device to said test signal.

3. The apparatus of claim 1 wherein said positioning means urges said fluid confining cell directly against said sensing layer so as to form a leakproof seal therebetween.

4. The apparatus of claim 1 further comprising filling means for automatically filling said fluid confining cell with said test fluid when said cell has been urged into engagement with said circuit device.

5. The apparatus of claim 1 wherein a sealing material is placed between said sensing electronic circuit device and said orifice of said cell so as to form an essentially leakproof seal.

6. The apparatus of claim 1 further comprising means for directing said fluid to flow across said sensing layer.

7. The apparatus of claim 1 wherein the temperature of said fluid is varied.

8. The apparatus of claim 1 further comprising microprocessor means for controlling said apparatus.

9. The apparatus of claim 1 further comprising controlling means for performing a series of tests of said sensing electronic circuit device employing differing fluids and for recording the response of the sensing circuit to said series of tests.

10. The apparatus of claim 1 wherein said fluid is a gas.

11. The apparatus of claim 1 wherein said sensing electronic circuit device comprises a programmable memory and said apparatus further comprises means for writing into said programmable memory a characteristic correction curve corresponding to the response of said sensing electronic circuit device to said test fluid.

12. The apparatus of claim 1 further comprising means for physically altering said sensing electronic circuit device to produce a different result in response to measurements made by said monitoring means.

13. The apparatus of claim 12 wherein said means for altering comprises a laser to trim a portion of said sensing electronic circuit device.

14. A method for testing a plurality of chemical and ionic sensing electronic circuits comprising the steps of:
 (a) aligning a first sensing electronic circuit device of a plurality of such sensing electronic devices on a continuous surface and a fluid confining cell with respect to one another such that said fluid confining cell is aligned with a sensing layer of said circuit device, said cell having at least one orifice and being capable of containing a test fluid when said orifice is urged against a continuous surface,
 (b) urging said orifice against said sensing layer so as to form a leakproof seal,
 (c) filling said fluid confining cell with a test fluid so that said test fluid contacts said sensing layer, and
 (d) measuring the response of said circuit device to said test fluid, to characterize said circuit device,
 (e) and then repeating the above steps (a) through (d) so that a plurality of other sensing electronic circuit devices on said continuous surface are tested in succession to permit measuring the response of each of the circuit device to said test fluid, to characterize each of the said circuit devices.

15. The method of claim 14 wherein each of said steps are automatically accomplished a plurality of times to carry out plural tests with respect to a particular circuit device, a plurality of differing test fluids being employed in said plural tests.

16. The method of claim 14 wherein said sensing electronic circuit device comprises a programmable memory and said method further comprises the step of writing into said programmable memory a characteristic correction curve responsive to the correlation of the response of said sensing electronic circuit device to said test fluid.

17. The method of claim 14 further comprising the step of causing said fluid to flow across said sensing layer.

18. The method of claim 14 wherein the temperature of said fluid is varied.

19. The method of claim 14 wherein said fluid is a gas.

20. The method of claim 14 comprising the further step of applying a test signal to said circuit device, and monitoring the response of said circuit device to said test signal.

21. The method of claim 14 further comprising the step of altering said sensing electronic circuit device responsive to the characterization of said circuit device, so as to alter the electrical signal produced by said sensing electronic circuit device.

22. The method of claim 21 wherein said altering step comprises the step of laser trimming a portion of said sensing electronic circuit device.

* * * * *